United States Patent
Ammann et al.

(10) Patent No.: US 7,924,017 B2
(45) Date of Patent: Apr. 12, 2011

(54) MEASURING DEVICE, MEASURING PROBE, AND METHOD OF OPERATING THE MEASURING DEVICE

(75) Inventors: Jürgen Ammann, Zürich (CH); Jiangdong Di, Zürich (CH); René Rissi, Bertschikon (CH); Antonio De Agostini, Bern (CH); Klaus-Dieter Anders, Oberrohrdorf (CH)

(73) Assignee: Mettler-Toledo AG, Greifensee (CH)

( * ) Notice: Subject to any disclaimer, the term of this patent is extended or adjusted under 35 U.S.C. 154(b) by 768 days.

(21) Appl. No.: 11/704,941

(22) Filed: Feb. 12, 2007

(65) Prior Publication Data

US 2007/0214872 A1   Sep. 20, 2007

(30) Foreign Application Priority Data

Feb. 14, 2006   (EP) .................................. 06101681

(51) Int. Cl.
  *G01N 27/02*   (2006.01)
  *G01N 27/27*   (2006.01)
(52) U.S. Cl. ........ 324/438; 324/448; 324/449; 204/400; 204/406; 73/53.01
(58) Field of Classification Search .................. 324/438, 324/448, 449
  See application file for complete search history.

(56) References Cited

U.S. PATENT DOCUMENTS

| | | | | |
|---|---|---|---|---|
| 3,657,094 | A * | 4/1972 | Hans et al. ..................... 204/408 |
| 5,046,028 | A * | 9/1991 | Bryan et al. ................... 702/116 |
| 5,809,518 | A | 9/1998 | Lee | |
| 6,119,508 | A * | 9/2000 | Tarui et al. .................... 73/53.01 |
| 6,142,959 | A * | 11/2000 | Sarvazyan et al. ............ 600/587 |
| 6,173,600 | B1 | 1/2001 | Harada et al. | |
| 6,653,842 | B2 * | 11/2003 | Mosley et al. ................ 324/446 |
| 6,747,473 | B2 * | 6/2004 | Cowan .......................... 324/765 |
| 6,831,571 | B2 * | 12/2004 | Bartel ......................... 340/854.6 |
| 7,704,357 | B2 * | 4/2010 | Pechstein et al. ............. 204/406 |
| 2002/0014410 | A1 * | 2/2002 | Silveri et al. .................. 204/412 |
| 2002/0171430 | A1 * | 11/2002 | Gehrke et al. ................ 324/438 |
| 2003/0132755 | A1 * | 7/2003 | Feng et al. .................... 324/438 |

FOREIGN PATENT DOCUMENTS

| | | |
|---|---|---|
| EP | 0 419 769 A2 | 4/1991 |
| EP | 0 497 994 A1 | 8/1992 |
| EP | 1 550 861 A1 | 7/2005 |
| JP | 61-173169 (A) | 8/1986 |
| WO | WO 92/21962 A1 | 12/1992 |

OTHER PUBLICATIONS

Mettler Toledo, Ingold Leading Process Analytics, Process Measurement Solutions Catalog, Jun. 2005, 4 pages.
Mettler Toledo, Ingold Leading Process Analytics, Prozessanalytische Systemlösungen, für die Brauerei, 20 pages.
European Search Report dated Apr. 18, 2006.

\* cited by examiner

*Primary Examiner* — Melissa J Koval
*Assistant Examiner* — John Zhu
(74) *Attorney, Agent, or Firm* — Buchanan Ingersoll & Rooney PC (57) ABSTRACT

The measuring device has at least one measuring probe, e.g., a physical or electrochemical measuring probe, which is equipped with one or more memory units and which is connected through a cable, e.g., a coaxial cable, to a transmitter which includes a processor. The measuring probe has a ground wire and is connected to the memory unit through a first signal wire, wherein under the control of the processor in accordance with a transmission protocol, the first signal wire and a connecting cable serve for the unidirectional transmission of the analog or digital measuring signal of the measuring probe as well as the preferably bidirectional transmission between the measuring probe and the transmitter of digital operating data which are read from or to be written into the memory unit.

41 Claims, 6 Drawing Sheets

MEASURING DEVICE, MEASURING PROBE, AND METHOD OF OPERATING THE MEASURING DEVICE

CROSS REFERENCE TO RELATED APPLICATIONS

This application claims priority under 35 U.S.C. §119 to EP Application 06101681.2 filed in European Patent Office on 14 Feb. 2006, the entire contents of which are hereby incorporated by reference in their entireties.

FIELD

A measuring system is disclosed with at least one measuring probe. A physical or electrochemical measuring probe can be used for the measuring device. A method of operating the measuring device is also disclosed.

BACKGROUND INFORMATION

The control of industrial processes, for example in the chemical and pharmaceutical industry, in the textile industry, in the food- and beverage industry, in the processing of paper and cellulose or in the water purification and waste water treatment is based on the measurement of process parameters which are determined with suitable measuring probes or sensors.

According to reference [1], "Process Measurement Solutions Catalog 2005/06", Mettler-Toledo GmbH, CH-8902 Urdorf, Switzerland, pages 8 and 9, a complete measuring system consists of a housing, a measuring probe, a cable and a measurement converter (also called a transmitter). By means of the housing, the measuring probe is brought into contact with the process that is to be measured or monitored, for example by immersing the probe in the process material and holding it there. The measuring probe serves to measure specific properties of the process. Through a cable which in the case of reference [1], page 8, has five leads the measuring signals are sent to the transmitter which, in turn, communicates with a process control system and converts the measuring signals into readable data. The measuring probes are selected depending on what properties of the process material need to be measured.

Reference [2], "Prozessanalytische Systemlösungen für die Brauerei" (*Process-Analytical Systems Solutions for the Brewery*), a company publication of Mettler-Toledo GmbH, CH-8902 Urdorf, Article No. 52 900 309, printed August/2003, describes as an example that in individual stages of the process chain of a brewery (consisting of the water purification stage, the brew house, the fermentation- and storage cellar, the filtration, carbonization and bottling, as well as the waste water treatment) measurements of electrical conductivity, dissolved oxygen, pH value, $CO_2$ value, and turbidity of the process material are performed by means of appropriate measuring probes.

An important factor for a problem-free process control is the condition of the measuring probes, whose properties will normally change over a longer operating time period.

A method disclosed in reference [3], EP 1 550 861 A1, serves to determine the condition of measuring probes which are integrated in a system with one or more stages and which are cleaned from time to time in state-of-the-art CIP- or SIP processes, i.e., without uninstalling the probe. According to this method, the temperature of the measuring probe or of the medium surrounding the measuring probe is measured by means of a sensor that is located inside or outside the measuring probe, and the condition of the measuring probe is determined from the time profile of the measurements of the temperature and in some cases of the process-related value (for example pH) that has been recorded during the operation of the measuring probe.

According to reference [4], WO 92/21962, the hydrogen ion concentration in liquids, i.e. the pH value, is often measured with glass electrodes. Preferably the condition of the glass electrodes is continuously monitored, as the measuring accuracy could become compromised for example if the ion-sensitive membrane is damaged, the diaphragm is contaminated, and if an electric connection inside the electrode is interrupted and/or short-circuited.

According to reference [4], a square pulse that is variable in amplitude and duration is applied with a high impedance to the measuring probe which contains a glass electrode as measuring electrode and also contains a reference electrode; the voltage across the measuring probe which has been changed by the probe impedance is measured and the measured values are compared to a reference value for a new measuring probe that has been determined by experiment or calculation. The square pulses in this arrangement are delivered by an analog output terminal of a processor and sent to the measuring probe by way of a separate conducting lead.

In the method described in reference [5], EP 0 419 769 A2, the monitoring is performed by means of symmetrical bipolar current pulses which are produced by a control unit. The duration of the current pulse periods is freely selectable and can be set to different lengths depending on the accuracy desired for checking the probe. This method requires a comparatively complex circuit, in particular two control leads which, for the purpose of generating symmetrical bipolar current pulses, allow switching between a positive voltage source and a negative voltage source, or switching from the measuring phase in which the pH value is measured to the checking phase in which the electrodes are checked.

A method disclosed in reference [6], EP 0 497 994 A1 relates to the checking of a pH-measuring probe which contains an auxiliary electrode in addition to the glass electrode and the reference electrode. Furthermore, there are two processing devices which are supplied, respectively, by a first and a second generator with an AC test voltage. The first generator in this arrangement operates with a frequency that is an integer multiple of the frequency of the second generator. This allows a separate monitoring of the glass electrode and the reference electrode. In the first case, the property being checked is the resistance of the chain formed of the glass electrode and the auxiliary electrode, while in the second case the resistance of the chain formed of the reference electrode and the auxiliary electrode is being checked. With the selected ratio between the frequencies produced by the generators, a sufficiently accurate differentiation is possible between the output signals in the two processing devices, as in each case one of the output signals is suppressed by the phase-sensitive rectification in the processing device of the other of the two electrodes. The processing devices are therefore no longer directly seeing the difference between the potentials of the glass electrode and the auxiliary electrode. Rather, they detect a difference between the potentials of the glass electrode and the auxiliary electrode or between the potentials of the reference electrode and the auxiliary electrode. As both of the differences in the potentials are referenced to the same potential of the auxiliary electrode, the potential difference between the glass electrode and the reference electrode can be determined with a differential amplifier. In this measuring circuit arrangement, the measuring probe therefore needs to be supplied with the AC test voltages of two different generators. These AC test voltages, in turn, are used for the subsequent phase-coherent processing of the signals and therefore have to be transferred through appropriate conductor leads which normally run from the processing unit to the measuring probe.

However, using additional conducting leads for transferring signals makes the design commensurately more expensive. Furthermore, in systems that are already installed, the required wiring does not exist and can hardly be retrofitted, or only at very high cost and by interrupting the operation of the equipment. This is also a disadvantage because with the trend towards miniaturization and the possibilities that it offers for a decentralized arrangement of intelligent components, the need for transmitting additional signals will rather increase, and more highly developed measuring probes designed for decentralized installation will therefore have only limited use in existing systems.

As was described above, in larger plants as for example breweries a large number of measuring probes are used. Thus, the way in which the installed measuring probes are administrated by the user is of high importance.

SUMMARY

An improved measuring device with at least one measuring probe and a method for operating the at least one measuring probe, as well as a suitable measuring probe, are disclosed.

In a measuring device measuring probes can be advantageously integrated. This means that when a new or previously used measuring probe is installed, the measuring process should register the measuring probe and should possibly be able to make required adaptations in the measuring probe and/or in the measuring process.

The monitoring of the measuring probes is to be further simplified and improved, taking into account extraneous influences and/or inherent properties of the measuring probe or changes of such properties.

An advantageous way of controlling the measuring probes can be realized with the exemplary embodiments.

Furthermore, the operation and administration of the measuring probes of the measuring system is to be simplified.

Accordingly, the infrastructure can be simplified for the transmission of signals which is provided in the measuring device or measuring system.

In exemplary embodiments, the measuring device should in addition remain compatible with conventional measuring probes.

Solutions to meet the foregoing objectives are offered by an exemplary measuring device, specifically a measuring system with at least one measuring probe, e.g., a physical or electrochemical measuring probe, by a measuring probe for use in the system, and by a method for operating the measuring device as disclosed.

The measuring device has at least one measuring probe equipped with at least one or with several memory units, by means of which process variables of a process material can be measured, for example electrical conductivity, dissolved oxygen, pH value, $CO_2$ value and/or turbidity. The measuring probe is connected through a cable, e.g., a coaxial cable, to a transmitter which includes a processor and can have several measuring probes-connected to it. The memory unit can be an overwritable solid-state memory, for example an EEPROM of the type Dallas Semiconductor DS 2433.

An exemplary measuring probe has a ground wire and is connected to the memory unit by a first signal wire. Under the control of the processor in accordance with a transmission protocol, the first signal wire and a corresponding signal wire of a connecting cable provide the communication between the measuring probe and the transmitter for the unidirectional transmission of the analog or digital measuring signal of the measuring probe as well as for the preferably bidirectional transmission of digital operating data that are to be read from or written into the memory unit. Thus, the analog or digital measuring signal as well as operating data can be transmitted through the signal wire and the ground connection of the measuring probe and through the signal wire and the ground connection of the cable that is connected to the measuring probe.

This has several advantages. For example, the cost and complexity of the installation are reduced since, instead of a multi-wire cable, only one cable can be used, e.g., a coaxial cable which contains the signal wire and, if the ground connection is not realized in another way, the ground wire. The term "wire" as used here encompasses physical electrical connections of any kind, besides wires in the actual sense of the word. Furthermore, installed measuring probes can be centrally controlled by the transmitter or, for example, by the lead computer. Every measuring probe can have its own globally unique identification code, which can have product properties assigned to it. Segments of e.g. a 64-bit code can serve to register for example the type of the probe (for example pH probe) and its serial number. With the identification code, the administration of all measuring probes of a system therefore becomes a simple task. The lead computer can for example access a database in which all data for the type of probe in question are registered. For example all performance characteristics, configuration data and operating parameters or operating programs can be registered, which can be updated by the manufacturer in periodic intervals. As a possible option, although with a higher cost, the storage of the foregoing data can be decentralized in the one or more memory units of the measuring probes.

In an exemplary embodiment, the first signal wire is connected to the reference electrode and a second signal wire is connected to the measuring electrode, or the first signal wire is connected to the measuring electrode and the second signal wire to the reference electrode of a measuring probe that serves for pH measurements, wherein the signals of the measuring electrode and of the reference electrode can in some cases be transmitted as analog signals through an impedance converter to the transmitter, where they may be processed by means of a differential amplifier. This kind of an arrangement allows the analog measuring signals to be processed in the transmitter, with only one additional signal wire being required in this case. In other words, with two signal wires it is possible to transmit two analog measuring signals as well as digital operating data.

This exemplary embodiment of the device can be realized by means of a coaxial coupler which has three contact elements which are concentric to each other and configured in the shape of rings, sleeves, cylinders, bushings, discs and/or pistons separated from each other by insulating layers and which can be connected to the cable through a further, corresponding coaxial coupler in such a way that the first signal wire connects to the core conductor, the second signal wire connects to the inner screen conductor, and the ground wire connects to the outer screen conductor of the coaxial cable which is connected to the transmitter.

With this exemplary embodiment, a known coaxial coupler of the type which has until now been used in measuring probes can be expanded in the sense that instead of only one contact connection for a screen conductor, two separate contact connections for screen conductors become available. The original contact connection for the screen conductor is in this case split in such a way into two separate contact segments that the resultant three-pole coaxial coupler of the measuring probe can be connected to a conventional two-pole coaxial coupler of a cable that is connected to the transmitter. When connected to the conventional two-pole coaxial coupler, the two screen conductor connections of the three-pole coaxial coupler are short-circuited, so that the memory unit of the measuring probe which is connected to these short-circuited contacts is not tied into the measuring device. New measuring probes are therefore compatible with existing systems and can be put into service already before the system itself is expanded.

In a further exemplary embodiment, the measuring probe is equipped with a processor which may be connected to the first signal wire through a parallel/serial converter component (for example Dallas Semiconductor type DS 2408) and may integrally include the at least one memory unit. The processor in this case has the capability for processing the measuring signals that were collected by means of the measuring probe and digitized and, if applicable, for writing corresponding digital data into, or reading such data out of, the at least one memory unit, and/or for configuring and/or controlling the measuring probe in accordance with the operating data provided by the transmitter.

These measures make it possible to control essential parts of the measuring and diagnostic processes within the measuring probe itself, whereby the centralized systems are relieved and the capacity and flexibility of the process system are significantly increased. For example, the physical structure and the centrally controlled administration and maintenance are simplified. By controlling the setting of operating parameters, it is possible to adapt and optimize the measuring probes when process conditions change. Particularly advantageous is the capability for using controllable measuring probes which are configured to meet requirements, To name an example, a controllable voltage generator (e.g. Dallas Semiconductor type DS 2890) is used in the measuring probe, which allows a selectable setting of a polarization voltage for example for oxygen-measuring electrodes.

The architecture of the digitally operating modules of the measuring device can be chosen selectively. For example, a single-wire bus architecture is used consistently inside the measuring electrode as well as between the measuring electrode and the transmitter. In this arrangement, the master processor, which can be located in the transmitter, can control the slave processor which can be arranged in the measuring probe. The master processor can be able to access all other digital single-wire modules, each of which can have a globally unique address, and e.g., to read data from the at least one memory unit. The probe processor in this exemplary arrangement can process data, for example status data of the measuring probe, and can store them in the memory unit which is typically interrogated in a cycle by the lead computer or the transmitter. If the master processor is connected through a parallel/serial converter component to the probe processor, the latter with at least one memory unit can be imbedded in a largely autonomous multi-bit environment. For this exemplary case, only the master processor and the slave- or probe processor would communicate with each other.

The communication through the single-wire bus can be according to a known data transmission protocol, e.g., of a kind that is described in reference [7], U.S. Pat. No. 5,809,518.

In a further exemplary embodiment, the measuring electrode and the reference electrode of the pH-measuring probe are each connected to separate input terminals of a multiplexer by way of respective impedance converters. As an alternative, the measuring electrode and the reference electrode of the pH-measuring probe are each connected to separate input terminals of a multiplexer by way of respective impedance converters, where in addition the output terminals of the impedance converters are also connected to the input terminals of a differential amplifier whose output, in turn, is connected to a further input of the multiplexer. From the measuring signals of the measuring electrode and the reference electrode, the differential amplifier forms a measuring signal that corresponds to the measured process variable, specifically to the pH value. The latter measuring signal, after it has bee digitized, can be transmitted through the single-wire bus to the transmitter. If the design concept does not include an analog differential amplifier, the difference is determined digitally in the processor that is arranged inside the measuring probe. In both cases (i.e., with or without differential amplifier), the measuring signals of the measuring electrode and the reference electrode can be evaluated separately in order to examine the condition of the measuring probe.

To perform this function, the processor of the measuring probe or a frequency generator controlled by the processor produces test signals such as square-wave signals of a first frequency or of first and second frequencies and delivers the test signals to the measuring electrode and/or to the reference electrode, and the resultant time profiles of the voltage at each of the electrodes is evaluated by means of the processor of the measuring probe in order to obtain status data of the measuring probe and in certain cases to store the data in the memory unit.

In yet a further exemplary embodiment, a temperature sensor in the measuring probe is connected to a further input of the multiplexer in order to determine temperature data of the measuring probe or of the medium surrounding the measuring probe and, by means of the processor of the measuring probe, to store the data in certain cases in the memory unit or to directly evaluate them, in order to determine load exposures or the condition of the measuring probe and/or to determine the magnitude of corrections to be applied to the measuring signals. Notably, contaminations can occur on measuring probes which are used for the monitoring of chemical or microbiological processes, whereby errors can be introduced in the result of the measurement. Contaminations will therefore have to be removed not only in the system of conduit pipes but also on the measuring probes in order to simultaneously ensure correct measurement results and the absolutely sanitary condition of the system. Because of the large number of measuring probes being used, they are normally not uninstalled for cleaning but are cleaned or sterilized in a CIP- or SIP procedure (where CIP stands for "Cleaning In Place" and SIP for "Sterilizing In Place").

An exemplary way to determine the resultant load exposures of the measuring probes is to compare the temperature with at least one threshold value and, after the threshold has been exceeded:
  a) to register a corresponding load exposure,
  b) to determine the cumulative sum of all load exposures and/or
  c) to determine the cumulative sum of all load exposures and, through a comparison with a permissible maximum value for the cumulative load exposure, to calculate a permissible remaining load exposure or remaining operating life.

For example, after a load exposure has been found, the registered remaining operating life of the measuring probe is commensurately reduced. The permissible remaining load exposure or remaining operating life is for example represented as the remaining permissible number of CIP- or SIP processes.

Status data and/or load exposure data can be transmitted directly, but can be stored in the memory unit and requested by the transmitter or the lead computer. If a malfunction of the measuring probe is detected, it can be signaled without delay. For example, a status interrogation occurs in short time cycle intervals to check for the presence of malfunction signals (for example whether an error bit has been set).

The operating data which can be transmitted from the measuring probe to the transmitter and in certain cases forwarded to the lead processor therefore can include identification data, characteristic data, configuration data, status data of the measuring probe, test data determined, e.g., during operation of the measuring probe, and/or load exposure data.

Operating data transmitted to the measuring probe can include updated configuration data and/or control data by means of which the measuring probe can be configured and/or controlled.

As mentioned above, the disclosure is not limited in its application to certain measuring probes but can be used for any measuring probes with one or more electrodes such as measuring and reference electrodes or measuring sensors.

Furthermore, the measuring probes or measuring sensors can be used to advantage not only in industrial plants but also in the measuring laboratory.

BRIEF DESCRIPTION OF THE DRAWINGS

The invention is explained hereinafter in more detail with reference to the drawings, wherein.

DETAILED DESCRIPTION

Figure 1:
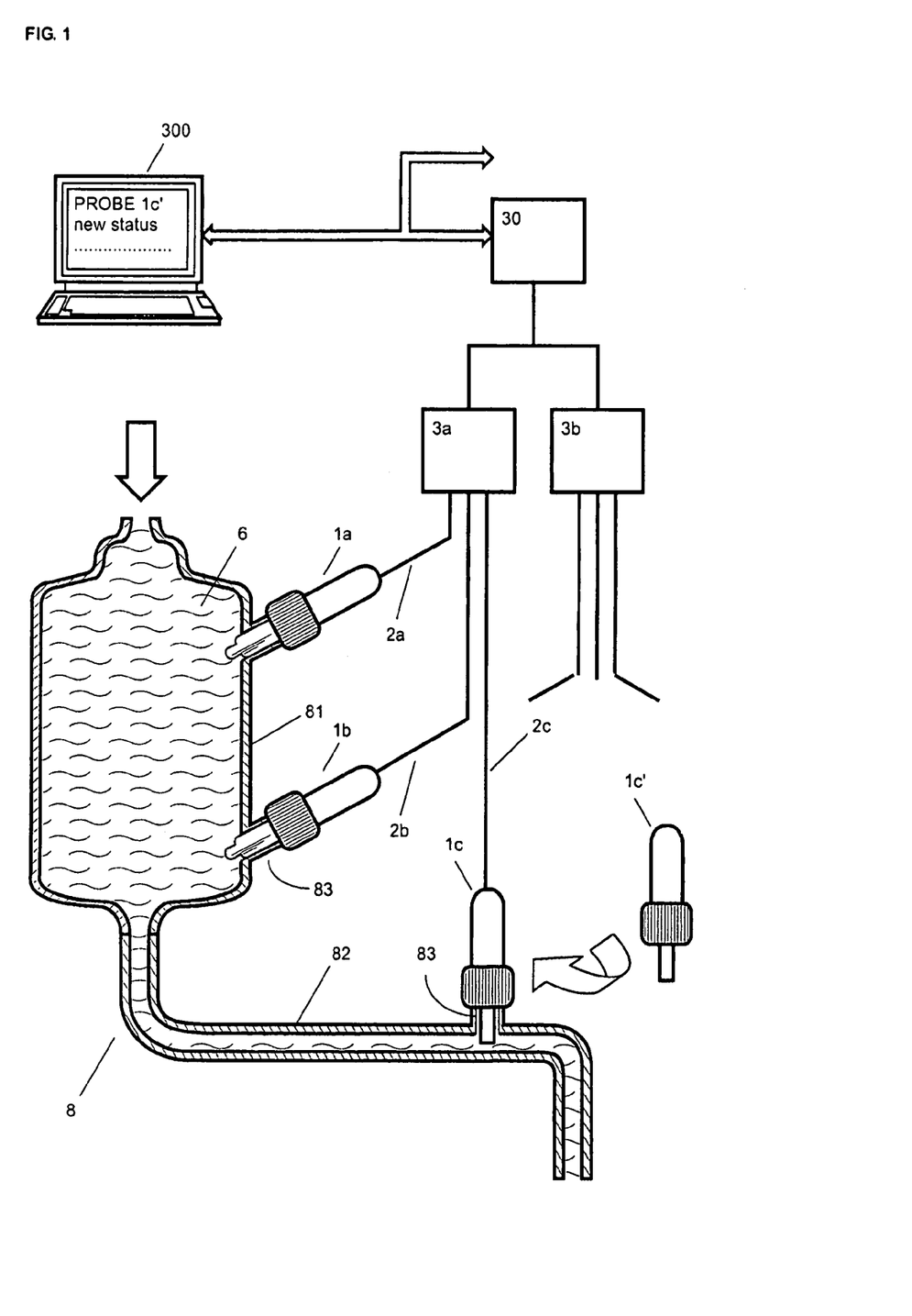
FIG. 1 represents an exemplary single-stage system with a container 8; 81, 82 and three integrally incorporated measuring probes 1a, 1b, 1c which are connected to a lead computer 300 through single-wire or dual-wire signal conductors 2a, 2b, 2c, a transmitter 3a, a segment coupler 30 and a bus system.

FIG. 1 illustrates a system with a material-holding portion 8 consisting of a container 81 filled with a process material 6, which may be connected by means of a connecting conduit pipe 82 to a system unit of a next-following process stage. The properties of the process material 6 are measured by means of exemplary measuring probes 1a, 1b, 1c, which are connected through single-wire and dual-wire signal conductors 2a, 2b, 2c—i.e. cables with one or two signal wires or electrical connections for signals and with a ground wire or ground connection—to a transmitter 3a or 3b which serves for example as a processing unit, a measurement converter, or in the simplest case as a relay station which exchanges data with the lead computer 300 by way of a segment coupler 30.

Figure 2:
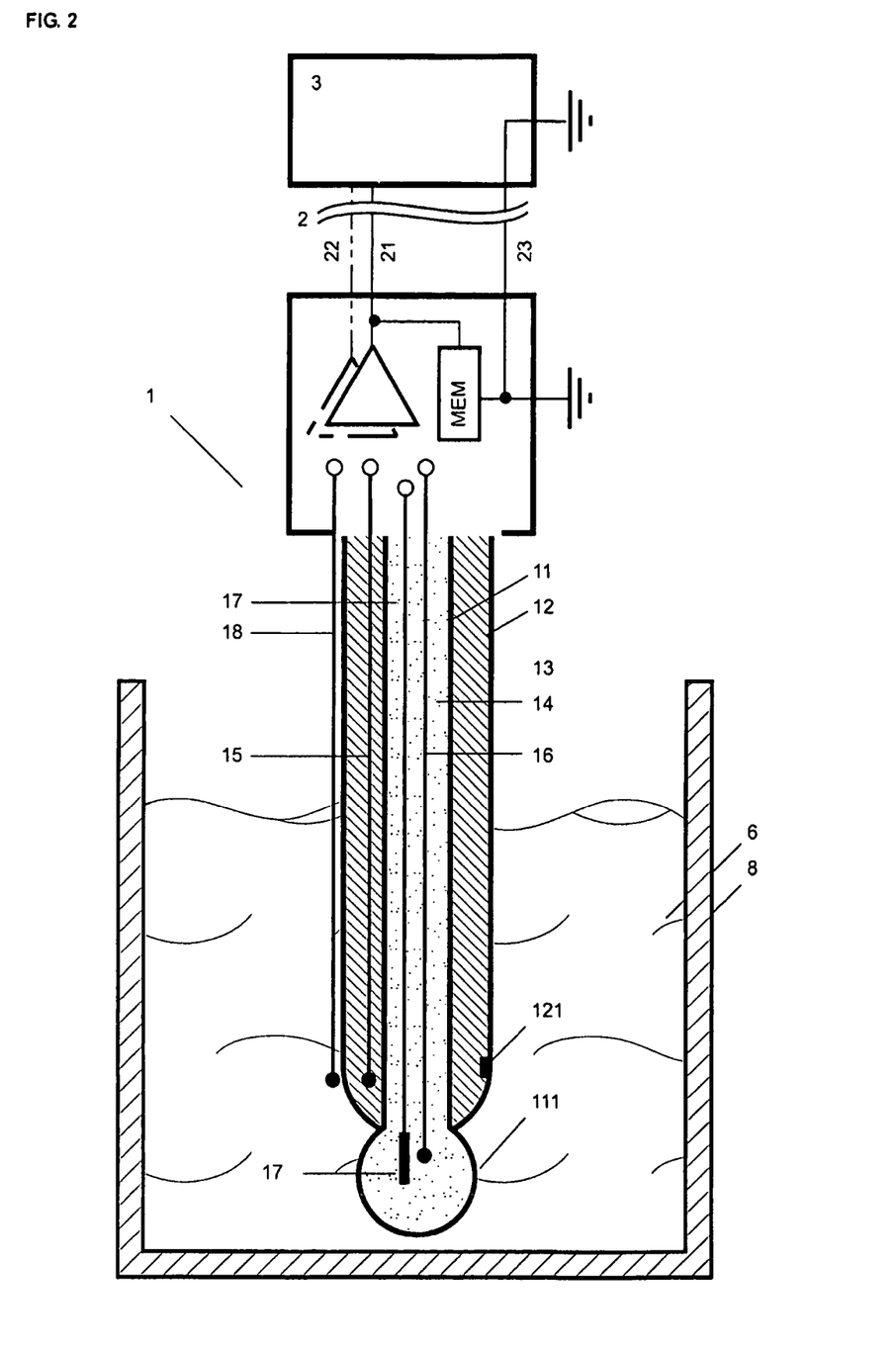
FIG. 2 represents an exemplary measuring device with a measuring probe 1, which is immersed in a liquid 6 to be measured and is connected to a transmitter 3 through a single-wire or dual-wire connection 2.

In a schematic illustration, FIG. 2 shows the principal structure of an exemplary pH-measuring probe which is configured as a single-rod measuring chain with a measuring electrode in the form of a glass electrode, with a reference electrode, and in certain cases also an auxiliary electrode 18. In the measuring probe 1, the glass electrode which includes a conductor element 16 and the reference electrode which includes a reference element 15 are built together in a unitary form of construction. In a first chamber inside an interior tube 11 which is joined to a thin-walled glass hemisphere or glass membrane 111, the conductor element 16 is immersed in a solution of a defined pH value, or an interior buffer solution 14, which establishes the conductive connection between the inside of the glass membrane 111 and the conductor element 16. Inside an exterior tube 12, the reference element 15 is immersed in an electrolyte, or an exterior buffer solution 13, which slowly diffuses through a porous separating wall or diaphragm 121 into the process medium 6. The voltage potential which is present at the conductor element 16 during the measurement (see FIG. 7, signal source $SQ1_G$) and the voltage potential which is present at the reference element 15 during the measurement (see FIG. 7, signal source $SQ1_R$) are transmitted through impedance converters and the two signal wires 21, 22 of the cable 2 to the transmitter 3. The measuring probe further has a memory unit MEM which is connected to the transmitter through one of the signal wires 21.

In this exemplary configuration of the measuring probe, there is further a temperature-measuring sensor 17 arranged in the interior buffer space, which in further exemplary embodiments of the measuring probe 1 allows temperature-related influence factors to be automatically compensated and temperature cycles to be registered.

Figure 3:
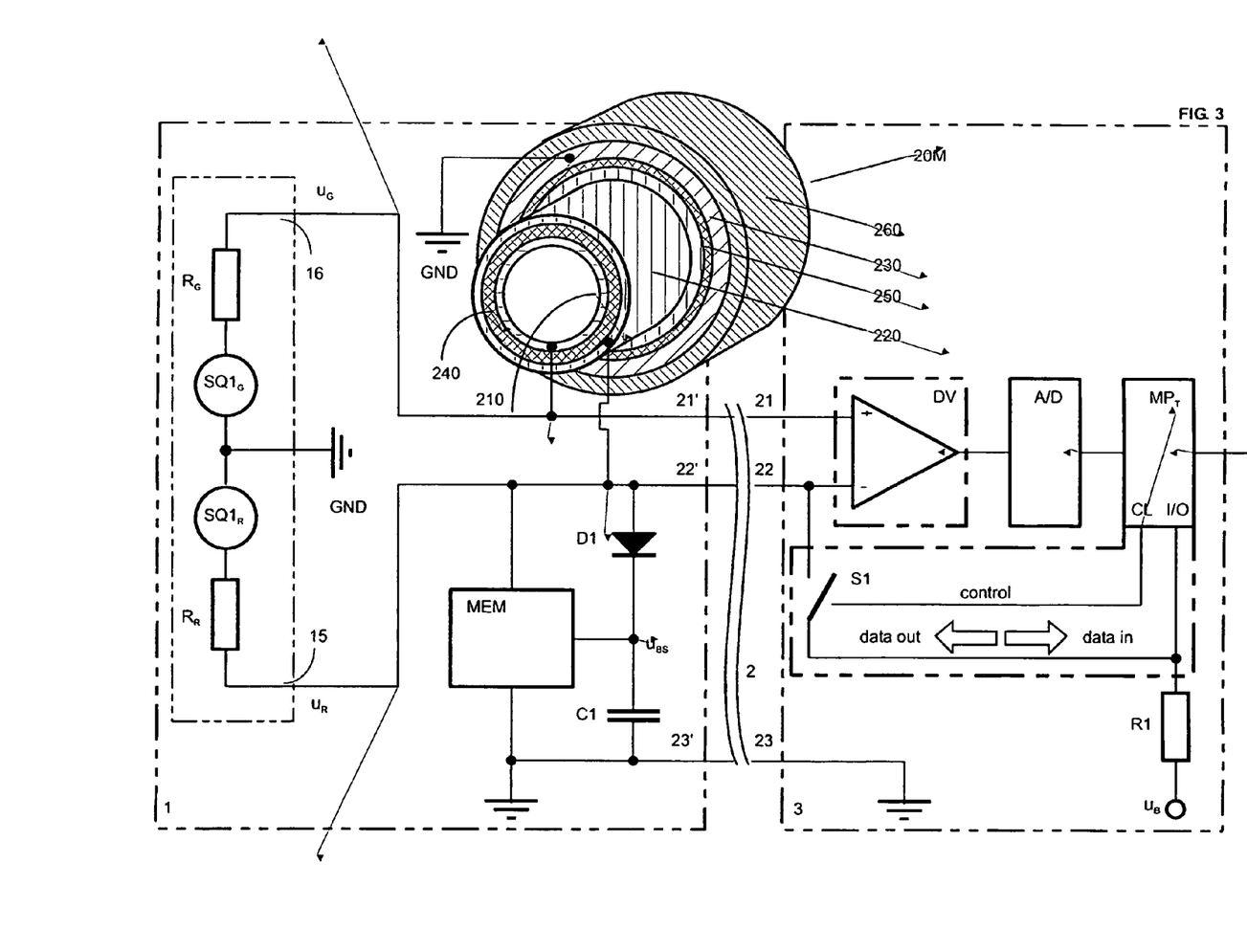
FIG. 3 represents the measuring device of FIG. 2 in an exemplary embodiment.

FIG. 3 shows the measuring device of FIG. 2 in an exemplary embodiment with a pH-measuring probe 1 which contains a glass electrode and a reference electrode where the respective voltages $u_G$ and $u_R$ appear as soon as the measuring probe 1 is immersed in the process medium or the material that is the subject of a measurement. The material 6 being measured and the glass membrane 111 together constitute the voltage source SQ1 whose internal resistance is determined primarily by the high resistance $R_G$ of the glass membrane 111. The voltages $u_G$ and $u_R$ are transmitted through the signal wires 21, 22 of the cable 2 to the input terminals of a differential amplifier DV which is part of the transmitter 3 and whose output is connected by way of an analog/digital converter A/D to a processor $MP_T$. Included in the measuring probe 1, which is further connected to the transmitter 3 through a ground wire 23, is a memory unit MEM (for example an EEPROM of the type Dallas Semiconductor DS 2433) which in this embodiment is connected to the processor $MP_T$ in the transmitter 3 by way of the second signal wire 22', 22 which serves as data bus. The processor $MP_T$ in this arrangement functions as bus master with the ability to access and to exchange data with the memory unit MEM which has a unique address. After the symbolically indicated switch S1 has been closed by the processor $MP_T$ by means of a control signal delivered through a control output terminal CL, a data transmission can take place through the second signal wire 22', 22 between the data port "I/O" and the memory unit MEM in the measuring probe 1. The switch S1 remains open, on the other hand, during the transmission of analog signals.

The transmission protocol provides for a sequential data transmission to take place after the circuit is initialized. While the processor $MP_T$ is active as bus master, it can address each of the components served by the signal wire 22', 22 or data bus 22', 22 and send data to, and/or receive data from, the component being addressed. For example a ROM component allows only the reading of data, an EEPROM allows data to be written into it and to be subsequently read back, a controllable voltage source POT (see FIG. 7) can receive control signals in order to set a voltage potential. In addition, there can be controllable switches for example to turn sensors or electrodes on and off or to switch over from one to another.

The voltage $u_{BS}$ which is required for the operation of the memory unit MEM and in certain cases further components is drained parasitically from the data bus 22, 22' by means of a diode D1 which charges a capacitor C1 as soon as a logic voltage is present on the data bus which is introduced from a voltage source $U_B$ by way of a resistor R1 and the closed switch S1.

The two signal wires 21', 22' running inside the measuring probe 1 as well as the ground wire 23' are connected to the contacts 210, 220, 230 of a three-pole coaxial coupler 20M which are separated from each other by insulating layers 240, 250. The coaxial coupler 20M can be connected by way of a matching coaxial coupler 20F (see FIG. 5) to the coaxial cable 2 in such a way that the first signal wire 21' is connected to the core conductor 21, the second signal wire is connected to the inner screen conductor 22, and the ground wire 23' is connected to the outer screen conductor 23 of the coaxial cable 2. The two outer contacts 220, 230 of the coaxial coupler 20M are divided into segments that lie in the same plane and are separated from each other by the insulating layer 250, so that they can connect to the corresponding contacts of the further coaxial coupler 20F when the two coaxial couplers 20M, 20F are plugged into each other. The two coaxial couplers 20M, 20F thus provide a reliable three-pole connection.

Figure 4:
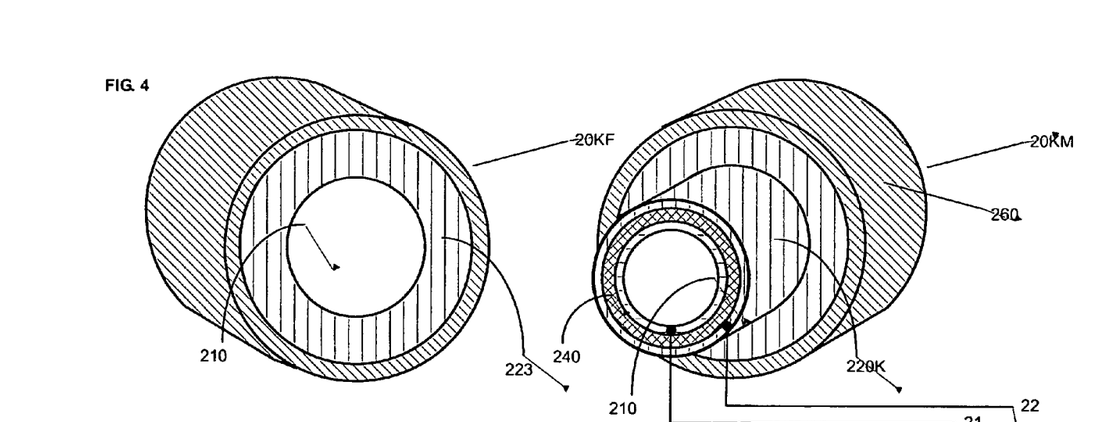
FIG. 4 represents known two-pole coaxial couplers 20KF and 20KM through which a measuring probe can be connected to a transmitter 3.

However, in many known systems, the connections between the measuring probe l' and the transmitter 3 are only of the two-pole kind with corresponding two-pole coaxial couplers 20KF, 20KM as shown in FIG. 4.

Figure 5:
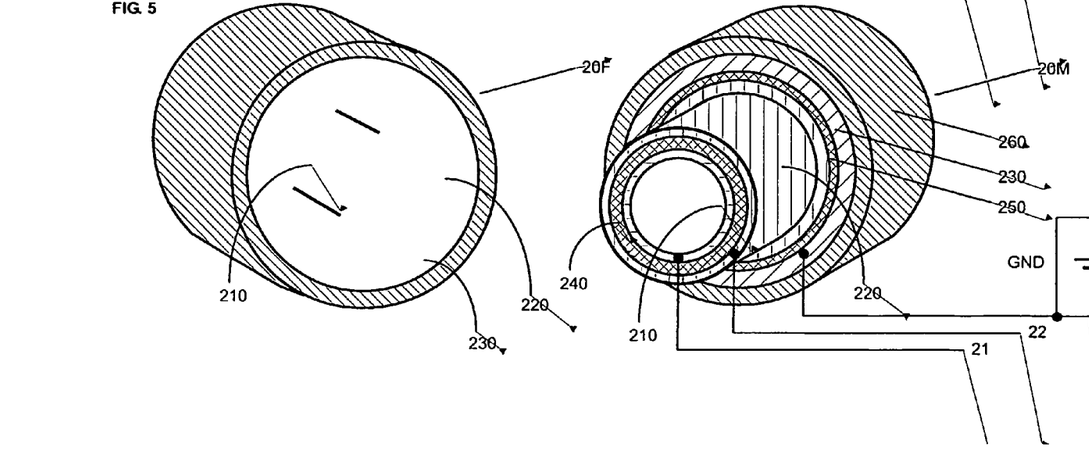
FIG. 5 represents exemplary three-pole coaxial couplers 20F and 20M, through which an exemplary measuring probe 1 can be connected to a transmitter 3.

The exemplary three-pole coaxial coupler 20M, which is shown in FIGS. 3 and 5, can now be mechanically and electrically connected to the three-pole coaxial coupler 20F of FIG. 5 as well as to a two-pole coaxial coupler 20KF (which is shown in FIG. 4), where in the latter case the two screen-conductor contacts 220 and 230 of the three-pole coaxial coupler 20M lie against the screen conductor contact 223 of the two-pole coaxial coupler 20KF and are thereby electrically connected to each other. Using the three-pole coaxial coupler 20M and the two-pole coaxial coupler 20KF, an exemplary measuring probe 1 can therefore be connected to a conventional transmitter that is not equipped for the transmission of digital data to the measuring probe 1. The memory unit MEM will in this case not be used.

This makes it possible for the manufacturer to produce only one kind of measuring probe which can be used universally for measuring devices and systems of the known type as well as the exemplary disclosed embodiments. The user gains the advantage of being able to purchase and use the exemplary measuring probes in an existing system already before it has been upgraded to work.

Figure 6:
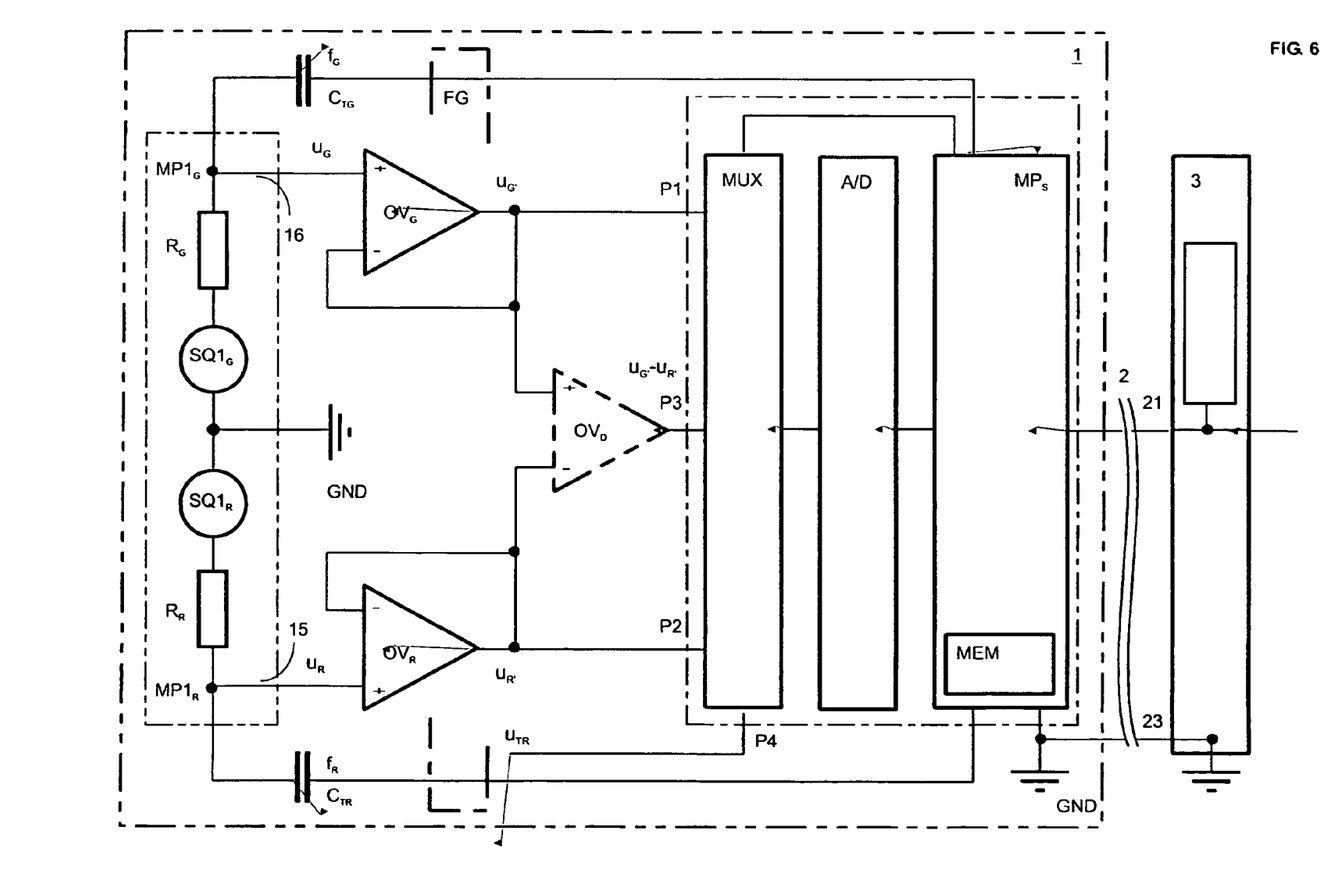
FIG. 6 represents an exemplary measuring device with an exemplary measuring probe 1, which includes a processor $MP_S$ equipped with the memory storage unit MEM and connected to a transmitter 3 by way of a single-wire connection 21.

FIG. 6 shows an exemplary measuring device with an exemplary measuring probe 1, where the measuring probe contains a processor $MP_S$ which has a memory unit MEM and is connected through a single-wire signal conductor 21 and the ground connection 23 of a cable 2 to a transmitter 3. Arranged in the transmitter ' 3 is the processor $MP_T$ which functions as bus master with the capability to exchange data with the slave- or probe processor $MP_S$ through the single-wire conductor 21 which serves as data bus.

The probe processor $MP_S$ is operable to receive the sequential transmission of the measuring signals $u_G$, $u_R$, $u_G - u_R$, and $u_{TR}$ which are produced by the measuring probe 1 and arrive at the probe processor $MP_S$ by way of a multiplexer MUX (which is controlled by the probe processor) and an immediately following analog/digital converter A/D. Of course, the multiplexer MUX, the analog/digital converter A/D and the probe processor $MP_S$ can also be integrated in a housing.

The glass electrode and the reference electrode of the measuring probe 1 which serves to measure pH are connected through respective impedance converters $OV_G$, $OV_R$ to the first and second input terminals P1 and P2 of the multiplexer MUX. The outputs of the impedance converters $OV_G$, $OV_R$ in addition can be connected to the input terminals of a differential amplifier $OV_D$ whose output, in turn, is connected to the third input terminal P3 of the multiplexer MUX. The fourth input terminal P4 of the multiplexer MUX receives the signal $U_{TR}$ of a temperature sensor (for example of the type PT100).

The digitized differential signal $u_{G'} - u_{R'}$ or, alternatively, the difference calculated by the probe processor $MP_S$ between the signals $u_{G'}$ and $u_{R'}$ after they have been digitized corresponds to the pH value of the process medium 6. Without further processing or after applying a correction if necessary, the probe processor $MP_S$ can send the digital difference value to the transmitter 3 and/or store it in the memory unit MEM which in this' exemplary embodiment is integrated in the probe processor $MP_S$.

By evaluating the further measuring signals $u_{G'}$ and $u_{R'}$ it is possible to determine the condition of the measuring probe 1. To make this determination, the processor $MP_S$ of the measuring probe, the processor $MP_T$ of the transmitter, or a frequency generator FG (indicated schematically) controlled by one of the processors produces test signals $f_G$, $f_R$ such as square-wave signals of a first frequency or of first and second frequencies and delivers the test signals, respectively, to the measuring electrode and to the reference electrode. The resultant time profiles of the voltages $u_{G'}$, $u_{R'}$ at the electrodes, which depend on the respective internal resistances $R_G$ and $R_R$ of the electrodes, are evaluated by means of the probe processor $MP_S$ in order to obtain status data of the measuring probe 1, which can then be stored in the memory unit MEM and/or transmitted immediately to the transmitter. If for example a glass breakage or a strong contamination has occurred, the internal resistances $R_G$, $R_R$ and the corresponding profiles of the voltages $u_{G'}$, $u_{R'}$ change and as a result, an operating irregularity or even a malfunction can be registered and/or reported to the central computer 300.

The temperature sensor 17 which is connected to the multiplexer MUX allows the collection of temperature data of the measuring probe 1 or of the medium 6 surrounding the measuring probe 1. By means of the probe processor $MP_S$, the data can be stored in the memory unit MEM or evaluated in the probe processor $MP_S$ itself in order to determine load exposures or the condition of the measuring probe and/or to determine the magnitude of corrections to be applied to the measuring signals.

By means of the diagnostic capability that is incorporated in the measuring probe 1, it is therefore possible to detect and register irregularities and defects as well as aging effects or load exposures of the measuring probe 1 and, if the situation requires it, to report them immediately.

The measuring and diagnostic functions of the measuring probe 1 can be performed in a largely autonomous way. The necessity of having to transmit test signals from the transmitter 3 through separate conductors to, and in some cases back from, the measuring probe 1 is avoided. The result of this concept is a measuring probe 1 that is easy to install and offers a wide-ranging functionality.

Figure 7:
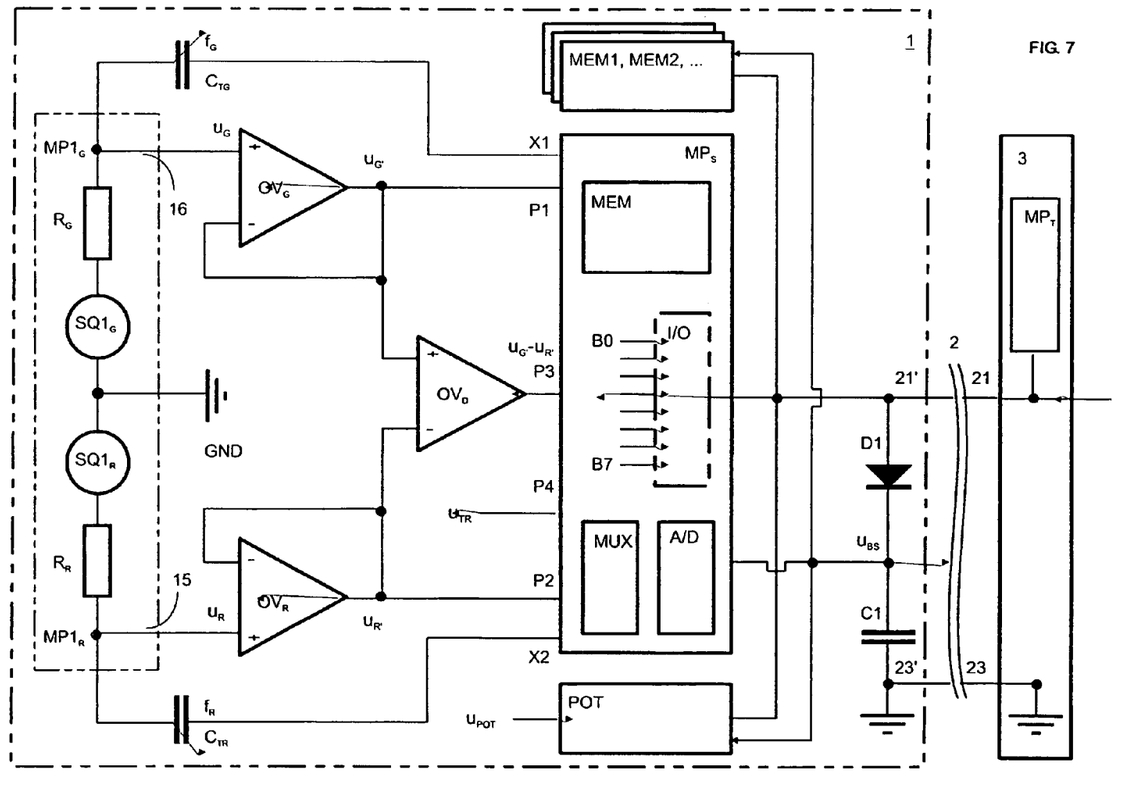
FIG. 7 represents the measuring device of FIG. 6 with a processor $MP_S$ in which a multiplexer MUX and an A/D converter A/D are integrated and which is connected by way of the single-wire signal conductor 21 to storage units MEM1, MEM2, ... and to a controllable voltage source POT.

FIG. 7 shows the measuring device of FIG. 6 with a probe processor $MP_S$ in which a multiplexer MUX and an analog/digital converter A/D are integrated and which is connected by way of the single-wire signal conductor 21 to memory units MEM1, MEM2, . . . , to a controllable voltage source POT as well as to the master processor $MP_T$ in the transmitter 3.

The master processor $MP_T$ can have the ability to communicate with all modules that are served by the single-wire bus 21, 21'. The operating protocol can include the provision that during a reserved time period the probe processor $MP_S$ can function as master processor for the single-wire bus 21, 21' either locally in the measuring probe 1 or globally in the measuring device, for example to store data in, or read data from, the memory units MEM1, MEM2, . . . . The memory units MEM1, MEM2, . . . can thus operate in a time-sharing mode. In the initialization, the probe processor $MP_S$ can work as local master processor, so that for example an operating program which is downloadable from the lead computer 300 and which may have been updated can be transferred by the probe processor $MP_S$ from the memory unit MEM1 into the internal memory MEM. This assures that the installed measuring probes 1 are always up-to-date with the latest state of the art available from the manufacturer.

FIG. 7 further illustrates schematically that in a further exemplary embodiment, a probe processor $MP_S$ with a larger bit format (for example an 8-bit processor) can be connected to the single-wire bus 21', 21 by way of a parallel/serial converter component (for example of the type Dallas Semiconductor DX 2408), which provides more flexibility in the selection of processors that can be used.

The advantages of an exemplary measuring device become particularly evident in a global view of a complex system (as shown partially in FIG. 1). On the one hand, by using exemplary measuring probes 1, the entire infrastructure for the data- and signal transmission is reduced while on the other hand important advantages are gained in the architecture, administration and servicing of the system.

Measuring probes 1 can be put in place and wired when the system is being installed, and they can subsequently be detected, identified and registered from a central location. Thus, the process control extends not only to the measuring function but also includes the administration of the measuring probes.

By registering the condition of the measuring probe 1, one gains an increase in process reliability. On the administrative side, the service activities including the placement of orders and the storage of the minimally required replacement probes can be precisely planned. As the installed measuring probes 1 can be reconfigured online, and with the possibility of even downloading operating programs online, the system is made highly flexible and easier to adapt to changes in the processes. After a measuring probe 1c has been replaced by a measuring probe 1c', a verification test can be performed immediately in the lead computer 300. The condition of the measuring probe 1c' can further be indicated on the transmitter 3 or, for example by means of light-emitting diodes, on the measuring probe 1c' itself.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LITERATURE REFERENCES

[1] "Process Measurement Solutions Catalog 2005/06", Mettler-Toledo GmbH, CH-8902 Urdorf, Switzerland
[2] "Prozessanalytische Systemlösungen für die Brauerei" (Process-Analytical Systems Solutions for the Brewery), company publication of Mettler-Toledo GmbH, CH-8902 Urdorf, Switzerland, Article No. 52 900 309, printed August/2003
[3] EP 1 550 861 A1
[4] WO 92/21962
[5] EP 0 419 769 A2
[6] EP 0 497 994 A1
[7] U.S. Pat. No. 5,809,518

The invention claimed is:

1. A measuring device, comprising:
   a housing;
   a measuring probe included in the housing, the measuring probe having a terminal in the housing and constituting an external interface to the housing;
   a transmitter external to the housing and including a first processor; and
   a cable connected to the first processor and the terminal,
   wherein the measuring probe comprises:
      at least one memory unit;
      a first signal wire connected to a terminal, which is configured to be connected to the first processor of the transmitter;
      a second processor configured to:
         process measuring signals of the measuring probe;
         communicate the processed measuring signals to the first processor of the transmitter via the first signal wire and the terminal;
         read operating data recorded in the at least one memory unit;
         transmit the read operating data to the first processor via the first signal wire and the terminal;
         receive operating data from the first processor via the first signal wire and the terminal; and
         write the received operating data into the at least one memory unit;
      a reference electrode;
      a measuring electrode;
      a multiplexer including a first input, a second input, and an output, the output of the multiplexer being connected to the second processor;
      a first impedance converter connected between the reference electrode and the first input of the multiplexer; and
      a second impedance converter connected between the measuring electrode and the second input of the multiplexer;
   wherein the multiplexer has a third input,
   wherein the measuring probe comprises a differential amplifier including a first input, a second input, and an output, the output of the differential amplifier being connected to the third input of the multiplexer, and wherein the first and second inputs of the differential amplifier are respectively connected to outputs of the first and second impedance converters.

2. The device according to claim 1, wherein the measuring probe is configured to measure values of at least one of conductivity, dissolved oxygen, pH, $CO_2$, and turbidity of a processed material, and produce the measuring signals to be representative of the measured values.

3. The measuring device according to claim 1, wherein the measuring probe comprises a parallel-to-serial converter component,
wherein the second processor is connected to the first signal wire through the parallel-to-serial converter component for serial transmission of at least one of the operating data and the processed measuring signals to the transmitter, and
wherein the second processor is configured to at least one of:
write the processed measuring signals into the at least one memory unit;
read the processed measuring signals out of the at least one memory unit;
control the measuring probe in accordance with the operating data received from the transmitter; and
configure the measuring probe in accordance with the operating data received from the transmitter.

4. The measuring device according to claim 1, wherein the measuring probe comprises an analog-to-digital converter configured to convert the measuring signals from an analog format to a digital format.

5. The measuring device according to claim 4, wherein the measuring probe comprises a temperature sensor configured to measure at least one of the measuring probe and a medium surrounding the measuring probe, and
wherein the second processor is configured to produce temperature data representative of the temperature measured by the temperature sensor, and to at least one of:
store the temperature data in the memory unit,
determine load exposures of the measuring probe,
determine condition information of the measuring probe, and
determine correction quantities for the measuring signals.

6. The measuring device according to claim 1, wherein the second processor is configured to produce test signals and to apply the test signals to at least one of the measuring electrode and the reference electrode, and
wherein the second processor is configured to evaluate time profiles of voltage present at at least one of the measuring and reference electrodes to determine status data of the measuring probe, the voltage resulting from the test signals applied to the at least one of the measuring and the reference electrodes.

7. The measuring device according to claim 6, wherein the multiplexer has a fourth input,
wherein the measuring probe comprises a temperature sensor connected to the fourth input of the multiplexer, the temperature sensor being configured to measure at least one of the measuring probe and a medium surrounding the measuring probe, and
wherein the second processor is configured to produce temperature data representative of the temperature measured by the temperature sensor, and to at least one of:
store the temperature data in the memory unit,
determine load exposures of the measuring probe,
determine condition information of the measuring probe, and
determine correction quantities for the measuring signals.

8. The measuring device according to claim 7, wherein the operating data comprises at least one of:
characteristic data transmitted from the measuring probe to the transmitter,
configuration data transmitted from the measuring probe to the transmitter,
status data of the measuring probe transmitted from the measuring probe to the transmitter,
test data transmitted from the measuring probe to the transmitter,
load exposure data transmitted from the measuring probe to the transmitter,
updated configuration data transmitted from the transmitter to the measuring probe, and
operation control data transmitted from the transmitter to the measuring probe that configures and/or controls the measuring probe.

9. The measuring device according to claim 6, wherein the measuring probe comprises a frequency generator controlled by the second processor to produce the test signals.

10. The measuring device according to claim 6, wherein the test signals comprise at least one of square-waves signals of a first frequency and square wave signals of first and second frequencies.

11. The measuring device according to claim 1, wherein the measuring probe comprises a circuit configured to transmit the measuring signals for processing by second processor, the circuit comprising an analog-to-digital converter that converts the measuring signals from an analog format to a digital format and at least one of a multiplexer, a direct connection, and an impedance converter connected to an input of the analog-to-digital converter.

12. The measuring device according to claim 1, wherein the operating data comprises at least one of:
characteristic data transmitted from the measuring probe to the transmitter,
configuration data transmitted from the measuring probe to the transmitter,
status data of the measuring probe transmitted from the measuring probe to the transmitter,
test data transmitted from the measuring probe to the transmitter,
load exposure data transmitted from the measuring probe to the transmitter,
updated configuration data transmitted from the transmitter to the measuring probe, and
operation control data transmitted from the transmitter to the measuring probe that configures and/or controls the measuring probe.

13. The measuring device of claim 1, wherein the second processor includes a multiplexer configured to transmit the measuring signals, an analog-to-digital converter configured to convert the measuring signals from analog format to digital format, and at least part of the at least one memory unit.

14. A measuring probe, configured to measure process parameters of a process material, comprising:
a housing;
at least one memory unit included in the housing;
a terminal included in the housing and configured to be connected to a transmitter external to the housing;
a first signal wire connected to the terminal in the housing; and
a processor included in the housing, the processor being configured to:
process measuring signals of the measuring probe;

communicate the processed measuring signals to the first processor of the transmitter via the first signal wire and the terminal;
read operating data recorded in the at least one memory unit;
transmit the read operating data to the first processor via the first signal wire and the terminal;
receive operating data from the first processor via the first signal wire and the terminal; and
write the received operating data into the at least one memory unit;
a reference electrode;
a measuring electrode;
a multiplexer including a first input, a second input, and an output, the output of the multiplexer being connected to the processor;
first impedance converter connected between the reference electrode and the first input of the multiplexer;
a second impedance converter connected between the measuring electrode and the second input of the multiplexer; and
a differential amplifier including a first input, a second input, and an output,
wherein the multiplexer has a third input connected to the output of the differential amplifier, and
wherein the first and second inputs of the differential amplifier are respectively connected to outputs of the first and second impedance converters.

15. The measuring probe according to claim 14, wherein the measuring probe is configured to measure values of at least one of conductivity, dissolved oxygen, pH, $CO_2$, and turbidity of a processed material, and produce the measuring signals to be representative of the measured values.

16. The measuring probe according to claim 14, comprising a parallel-to-serial converter component, wherein the processor is connected to the first signal wire through the parallel-to-serial converter component,
wherein the processor is configured for writing data into or reading data out of the at least one memory unit, and
wherein the first signal wire is configured as a data bus between different digital components, the different digital components including the processor and the transmitter.

17. The measuring probe according to claim 16, comprising:
a circuit configured to transmit the measuring signals for processing by processor, the circuit comprising an analog-to-digital converter that converts the measuring signals from an analog format to a digital format and at least one of a multiplexer, a direct connection, and a preamplifier connected to an input of the analog-to-digital converter.

18. The measuring probe according to claim 17, comprising a temperature sensor, and
wherein the second processor is configured to process temperature data from the temperature sensor, the temperature data being indicative of a temperature of the measuring probe or for the medium surrounding the measuring probe to at least one of:
store the temperature data in the memory unit,
determine load exposures of the measuring probe,
determine condition information of the measuring probe, and
determine correction quantities for the measuring signals.

19. The measuring probe according to claim 14, wherein the processor is configured to produce test signals and to apply the test signals to at least one of the measuring electrode and the reference electrode, and
wherein the processor is configured to evaluate time profiles of voltage present at at least one of the measuring and reference electrodes to determine status data of the measuring probe, the voltage resulting from the test signals applied to the at least one of the measuring and the reference electrodes.

20. The measuring probe according to claim 19, comprising a temperature sensor,
wherein the multiplexer has a fourth input connected to the temperature sensor, the temperature sensor being configured to measure at least one of the measuring probe and a medium surrounding the measuring probe,
wherein the processor is configured to produce temperature data representative of the temperature measured by the temperature sensor, and to at least one of:
store the temperature data in the memory unit,
determine load exposures of the measuring probe,
determine condition information of the measuring probe, and
determine correction quantities for the measuring signals.

21. The measuring probe according to claim 20,
wherein the operating data comprises at least one of characteristic data, configuration data, status data of the measuring probe, test data, load exposure data, updated configuration data, and operation control data that configures and/or controls the measuring probe.

22. The measuring probe according to claim 21,
comprising at least one voltage source configured to generate at least one operating voltage based on signals transmitted through the first signal wire.

23. The measuring probe according to claim 20, comprising a frequency generator controlled by the processor to produce the test signals.

24. The measuring probe according to claim 19, wherein the test signals comprise at least one of square-waves signals of a first frequency and square wave signals of first and second frequencies.

25. The measuring probe according to claim 14, comprising:
a circuit configured to transmit the measuring signals for processing by second processor, the circuit comprising an analog-to-digital converter that converts the measuring signals from an analog format to a digital format and at least one of a multiplexer, a direct connection, and a preamplifier connected to an input of the analog-to-digital converter.

26. The measuring probe according to claim 14, wherein the operating data transmitted from the measuring probe to the transmitter comprises at least one of characteristic data, configuration data, status data of the measuring probe, test data determined during operation of the measuring probe, load exposure data, and
the operating data stored in the at least one memory unit comprises at least one of updated configuration data and operation control data through which the measuring probe is configured and/or controlled.

27. The measuring probe according to claim 14, comprising at least one voltage source configured to generate at least one operating voltage based on signals transmitted through the first signal wire.

28. The measuring probe of claim 14, wherein the processor includes a multiplexer configured to transmit the measuring signals, an analog-to-digital converter configured to convert the measuring signals from analog format to digital format, and at least part of the at least one memory unit.

29. A method of controlling a measuring device, the measuring device comprising a measuring probe including a housing and a processor within a housing of the measuring probe, the processor being configured to process parameters of a process material and to communicate with a transmitter external to the housing of the measuring probe, the measuring probe comprising a reference electrode and a measuring electrode, the method comprising:
- processing, by the processor, measuring signals of the measuring probe;
- communicating, by the processor, the processed measuring signals to the transmitter;
- reading, by the processor, operating data recorded in a computer-readable medium of the measuring device
- transmitting, by the processor, the read operating data to the transmitter;
- receiving, by the processor, operating data from the transmitter;
- writing, by the processor, the received operating data into the computer readable medium of the measuring device;
- converting measuring signals of the reference electrode by an impedance converter;
- converting measuring signals of the measuring electrode by an impedance converter;
- choosing, by a multiplexer, to input to the processor for processing one of an output of the impedance converter of the reference electrode and an output of the impedance converter of the measuring electrode; and
- determining a difference between the output of the impedance converter of the reference electrode and the output of the impedance converter of the measuring electrode,
- wherein the step of choosing, by the multiplexer, includes choosing to input to the processor for processing one of the output of the impedance converter of the reference electrode, the output of the impedance converter of the measuring electrode, and the difference.

30. The method according to claim 29, comprising:
- converting at least one of the operating data and processed measuring signals from a parallel format to a serial format;
- serially transmitting the converted at least one of the operating data and processed measuring signals to the transmitter; and
- performing at least one of:
  - writing the processed measuring signals into the at least one memory unit;
  - reading the processed measuring signals out of the at least one memory unit;
  - controlling the measuring probe in accordance with the operating data provided by the transmitter; and
  - configuring the measuring probe in accordance with the operating data provided by the transmitter.

31. The method according to claim 30, comprising:
- transmitting the measuring signals for processing by the processor through at least one of a multiplexer, a direct connection, and a preamplifier; and
- converting the transmitted measuring signals from an analog format to a digital format.

32. The method according to claim 29, comprising:
- producing test signals in the measuring probe;
- applying the test signals to at least one of the measuring electrode and the reference electrode;
- evaluating time profiles of voltage present at at least one of the measuring and reference electrodes to determine status data of the measuring probe, the voltage resulting from the test signals applied to the at least one of the measuring and the reference electrodes.

33. The method according to claim 32, wherein the measuring probe comprises a temperature sensor, the temperature sensor being configured to measure at least one of the measuring probe and a medium surrounding the measuring probe; and the method further comprises:
- producing, by the processor, temperature data representative of the temperature measured by the temperature sensor, and
- performing at least one of:
  - storing the temperature data in the memory unit,
  - determining load exposures of the measuring probe,
  - determining condition information of the measuring probe, and
  - determining correction quantities for the measuring signals.

34. The method according to claim 33, wherein the operating data comprises at least one of:
- characteristic data transmitted from the measuring probe to the transmitter,
- configuration data transmitted from the measuring probe to the transmitter,
- status data of the measuring probe transmitted from the measuring probe to the transmitter,
- test data transmitted from the measuring probe to the transmitter,
- load exposure data transmitted from the measuring probe to the transmitter,
- updated configuration data transmitted from the transmitter to the measuring probe, and
- operation control data transmitted from the transmitter to the measuring probe that configures and/or controls the measuring probe.

35. The method according to claim 34, comprising:
- forwarding the transmitted operating data from the transmitter to a lead computer;
- performing, by the lead computer, at least one of monitoring, controlling, and servicing the measuring device for a.

36. The method according to claim 35, comprising:
- transmitting, by the lead computer, the operating data to be received by the processor of the measuring probe to reconfigure and/or to control the measuring probe for the measuring process.

37. The method according to claim 32, wherein the test signals comprise at least one of square-waves signals of a first frequency and square wave signals of first and second frequencies.

38. The method according to claim 29, wherein the measuring probe is configured to measure values of at least one of conductivity, dissolved oxygen, pH, $CO_2$, and turbidity of a processed material, and
- wherein the processed measuring signals communicated by the processor are representative of the measured values.

39. The method according to claim 29, transmitting the measuring signals for processing by the processor through at least one of a multiplexer, a direct connection, and an impedance converter; and
- converting the transmitted measuring signals from an analog format to a digital format.

40. The method according to claim 29, wherein the operating data comprises at least one of:
  characteristic data transmitted from the measuring probe to the transmitter,
  configuration data transmitted from the measuring probe to the transmitter,
  status data of the measuring probe transmitted from the measuring probe to the transmitter,
  test data transmitted from the measuring probe to the transmitter,
  load exposure data transmitted from the measuring probe to the transmitter,
  updated configuration data transmitted from the transmitter to the measuring probe, and
  operation control data transmitted from the transmitter to the measuring probe that configures and/or controls the measuring probe.

41. The method according to claim 29,
  transmitting, by a lead computer, at least one of the operating data, configuration data, and operating programs to be received by the processor of the measuring probe to reconfigure and/or to control the measuring probe for the measuring process.

* * * * *